(12) United States Patent
Calleri

(10) Patent No.: US 10,145,835 B2
(45) Date of Patent: Dec. 4, 2018

(54) SITE ANALYSIS SYSTEM FOR THE CALCULATION OF THE ISOTOPE RATIO OF THE CARBON IN SEVERAL GAS SPECIES BY MEANS OF A SINGLE ANALYSER

(71) Applicant: Geolog Srl, San Giuliano Milanese (MI) (IT)

(72) Inventor: Antonio Calleri, Milan (IT)

(73) Assignee: GEOLOG S.R.L., San Giuliano Milanese (MI) (IT)

( * ) Notice: Subject to any disclaimer, the term of this patent is extended or adjusted under 35 U.S.C. 154(b) by 158 days.

(21) Appl. No.: 15/237,626

(22) Filed: Aug. 15, 2016

(65) Prior Publication Data

US 2016/0356759 A1 Dec. 8, 2016

Related U.S. Application Data

(62) Division of application No. 13/617,276, filed on Sep. 14, 2012.

(51) Int. Cl.
*G01N 33/28* (2006.01)
*G01N 30/84* (2006.01)
*G01N 30/88* (2006.01)

(52) U.S. Cl.
CPC ......... *G01N 33/2823* (2013.01); *G01N 30/84* (2013.01); *G01N 30/88* (2013.01); *G01N 2030/8868* (2013.01)

(58) Field of Classification Search
CPC .......... G01N 2030/8868; G01N 30/84; G01N 33/2823; G01N 30/88
See application file for complete search history.

(56) References Cited

U.S. PATENT DOCUMENTS

| 2006/0021940 A1* | 2/2006 | Bertoncini | G01N 30/88 |
| | | | 210/656 |
| 2010/0055802 A1* | 3/2010 | Zare | G01N 21/39 |
| | | | 436/158 |

* cited by examiner

*Primary Examiner* — Dennis White
*Assistant Examiner* — Bryan Kilpatrick
(74) *Attorney, Agent, or Firm* — John Alumit

(57) ABSTRACT

The present invention relates to a system of analysis, which can be used in a mobile laboratory in a drilling site situation or in a similar situation, suitable for measuring (preferably in relation to at least two partially gaseous species, which derive preferably from a mixture extracted from a drilling mud, for example, methane, ethane, propane and/or any other heavier hydrocarbons) the quantities of the different isotopes of at least a same chemical element (preferably the quantities of $^{13}C$, carbon isotope with 6 protons and 7 neutrons, and of $^{12}C$, carbon isotope with 6 protons and 6 neutrons, respectively) by means of a laser isotopes analyzer regulated for a single, at least partially gaseous species which contains said chemical element.

1 Claim, 4 Drawing Sheets

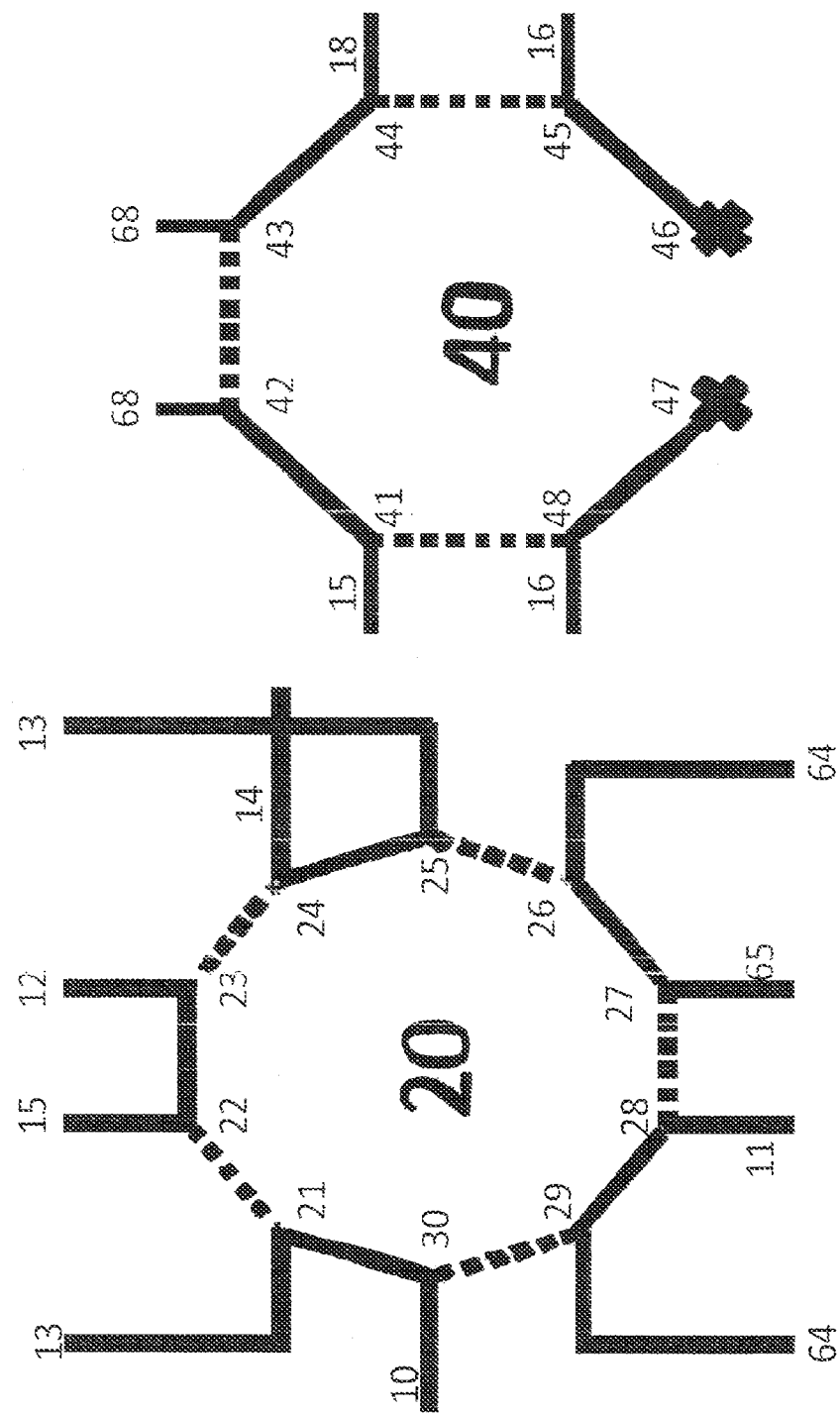

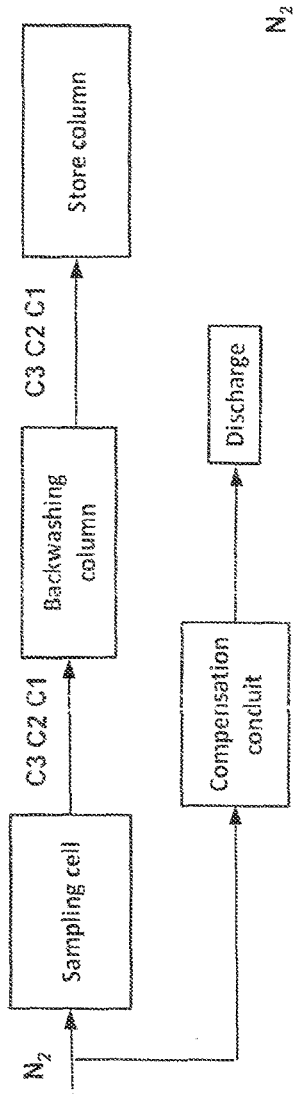
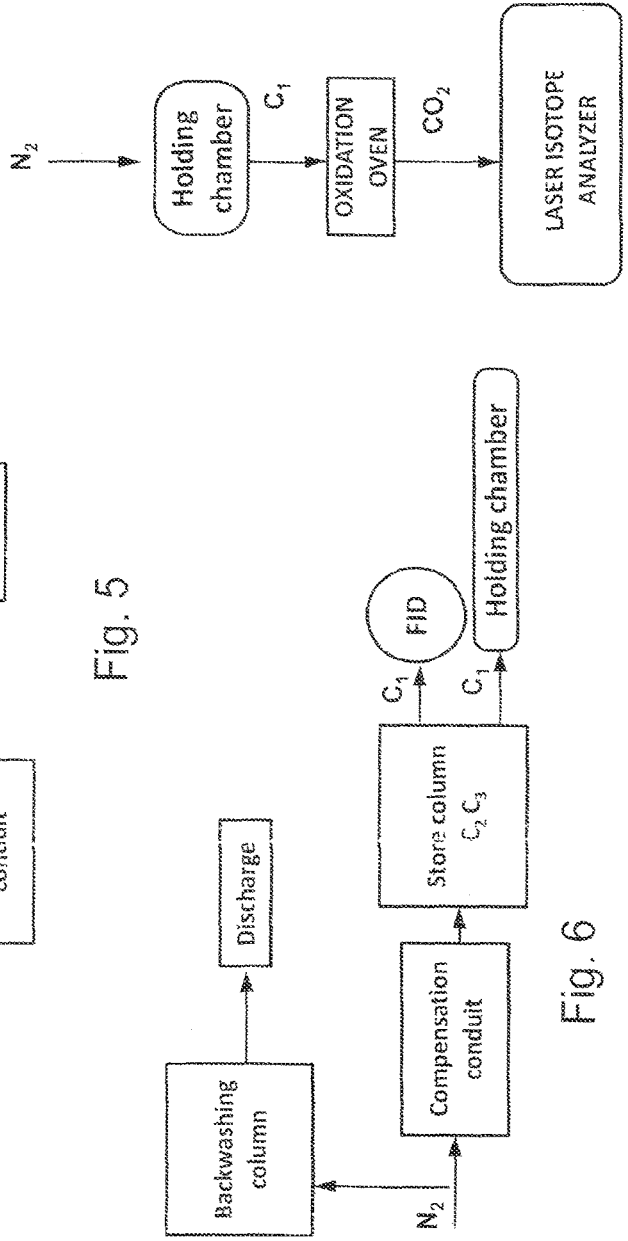
Fig. 5
Fig. 6
Fig. 7

SITE ANALYSIS SYSTEM FOR THE CALCULATION OF THE ISOTOPE RATIO OF THE CARBON IN SEVERAL GAS SPECIES BY MEANS OF A SINGLE ANALYSER

CROSS-REFERENCE TO RELATED APPLICATION

This application claims the benefit of U.S. patent application Ser. No. 13/617,276 filed on Sep. 14, 2012, which is currently pending. The earliest priority date claimed is Sep. 14, 2011.

FEDERALLY SPONSORED RESEARCH

None

SEQUENCE LISTING OR PROGRAM

None

BACKGROUND OF THE INVENTION

The present invention relates to a system of analysis, which can be used in a mobile laboratory in a drilling site situation or in a similar situation, suitable for measuring (preferably in relation to at least two at least partially gaseous species, which derive preferably from a mixture extracted from a drilling mud, for example, methane, ethane, propane and/or any other heavier hydrocarbons) the quantities of the different isotopes of at least a same chemical element (preferably the quantities of $^{13}C$, carbon isotope with 6 protons and 7 neutrons, and of $^{12}C$, carbon isotope with 6 protons and 6 neutrons, respectively) by means of a laser isotopes analyser regulated for a single, at least partially gaseous species which contains said chemical element.

At the current state of the art, the instruments which are commonly used for measuring the isotope ratio of carbon in hydrocarbons, which is linked to the quantities in mass of the two isotopes mentioned, are mass spectrometers of the IRMS (isotope ratio mass spectrometer) type, which in fact allows for separate investigation of the relative concentration of stable isotopes, $^{12}C$ and $^{13}C$, in different gaseous species. However, instruments of this type are not suitable for site analysis because of their dimensions and because they have to be used in particular environmental conditions free from vibrations and with stable temperature and pressure. These facts preclude their use in drilling sites, both on land and at sea, where said analysis has to take place in a continuous process.

The object of the present invention is that of producing a system of analysis which is able to measure the isotopic content of a chemical element, as a continuous process on site, and in relation to at least two different, partially gaseous species containing that element. Said species is contained in at least one partially gaseous mixture, which in turn was originally extracted, preferably from drilling mud. This allows accurate analyses to be carried out in a continuous and easily manageable manner, even in difficult environmental conditions, such as remote site locations on land or on a sea platform.

Another type of instrumentation for analysing the isotope ratio of carbon is known and described in patent application EP 1887342. This application is based on laser optical spectrometry, which allows the production of an instrument of simpler application and management and which can be used on site. However, because this instrument is configured in such a way that the laser spectrometer is able to quantify the relative abundance of the two stable isotopes of the carbon only in a single hydrocarbon species, it is not possible to analyse, the relative abundance of the two stable isotopes of the carbon also in other hydrocarbon species in a single analysis cycle and without modifying the configuration of the same laser spectrometer. In fact, the operation of changing the configuration of the analyzer leads to an unacceptable discrepancy between the analysis and the current depth.

Another object of the present invention is that of producing an instrument that is able to quantify the isotope ratio of a chemical element contained in at least two partially gaseous species in a continuous process on site. The partially gaseous species derive from a mixture previously contained in a drilling mud, without modifying the configuration of the isotope analyser. Thus, there is a good correlation between the analysis and the current depth. The latter analyser uses laser spectrometry and is intended to measure the relative quantity of two stable isotopes of a chemical element contained in each of said gaseous species. The gaseous species are previously separated from the mixture by means of a gas chromatograph controlled by software, and then transformed one by one into a gas species, such as carbon dioxide $CO_2$, for which this analyser is configured. In this way, the isotope content of several gaseous species can be analysed, continuously and at different depths, without having to work on the analyser. Such an operation would take too much time for numerous analyses, which cannot be prolonged excessively because the analyses have to be correlated to the depth in approximate real time considering that the mixture flows continuously.

Moreover, at the state of the art, no site instrument for the analysis of the isotope ratio of carbon in hydrocarbon gases internally provides a system of chromatographic separation of each gaseous species constituting the mixture sampled and comprising a flame ionization detector or FID. This detector was introduced in order to check the correct separation of the single gas species, and therefore to define the correct sampling thereof before carrying out the analysis. Without the flame ionization detector, the instrument would be considered "blind" and therefore not able to ensure that the same gas species is sampled in every phase in which the analysis is to be performed.

A further object of the present invention is that of producing an instrument which is able to quantify, also in a continuous process on site, at least one isotope ratio of a chemical element contained in at least two partially gaseous species. The partially gaseous species derives from at least a mixture previously contained in drilling mud. The instrument is able to ensure that the gas species is exactly the same in every phase whereof in which the analysis is performed.

To date, it has not been possible to perform isotope analyses of continuous flows sufficiently in real time by means of laser isotopes analysers. This is because it was not possible to have sufficiently distanced times in sending a single gas species to said analyser so as to allow the laser isotope analysis. In any case, it was not possible to conclude the cycle of analysis in a sufficiently rapid manner for all the gaseous species of geological interest, which are usually methane, ethane and propane.

Therefore, an important object of the present invention is that of providing an instrument with which it is possible to send single gaseous species extracted from a mixture which flows continuously, to a laser analyser at sufficiently large intervals of time, and which can rapidly conclude the entire cycle of analysis for all the gaseous species of interest in order to perform several analyzes in real time. Thanks to the particular configuration given here to the gas chromatograph, the gaseous species to be analysed are sent to the isotope analyser at sufficiently distanced intervals of time, so as to allow the same to perform the analysis of each individual species. All the gas species not yet analysed remain trapped in a column of the gas chromatograph, while only one of these species is sent towards the analyser, in such a way as to obtain a sufficient interval of time between two successive analyses. In any case, the device takes a sufficiently reduced time to conclude the entire cycle of analysis of the gas species extracted at a certain depth, and in such a way that it is possible to perform analyses at many levels of depth.

On these bases, the present invention uses the technology known as gas chromatography for the separation of gaseous species, combined with a flame ionization detector (FID). The FID is intended to correctly identify the times of gas retention under investigation inside the various components of the gas chromatograph. Gas chromatography, together with laser spectrometry, is used to detect the isotopic content, and so the isotopic ratio, of the carbon contained in each of said gaseous species.

SUMMARY OF THE INVENTION

Firstly, it is noted that, in the present application, and thus with reference also to the claims:
the term "valve" can denote any means for distributing at least one fluid flow and which preferably allows, on the bases of the configuration it takes on, the placing in contact, according to several combinations, of at least two sections or ways or outlets formed therein;
the term "conduit" can denote any means for the containing of at least one fluid flow;
the term "chromatographic column" can denote any means capable of separating at least partially, preferably on the bases of different weight, at least two gaseous species flowing in the same column;
the term "processor" can denote a software together with all the physical devices, which constitute the hardware and which allow the software to operate.

The present invention is, therefore, a system of analysis that is able to:
separate at least two different partially gaseous species from a mixture and extracted from drilling mud to be analyzed, such as methane, ethane and/or propane, as well as other possible superior equivalents including aromatic hydrocarbons;
quantify at least two different isotopes and optionally at least one isotope ratio of at least one chemical element for at least two of said gaseous species, which is preferably carbon, and coming from the latter species to be analyzed.

The instrument developed as part of the present invention is therefore constituted mainly at least by the following components:
at least one gas chromatograph for the mutual separation of said gaseous species;
at least one oxidation oven for heating separated gaseous species and consequently producing at least one other partially gaseous species;
at least one laser isotopes analyser configured to analyse said gaseous species produced by heating;
means for transferring each of said gaseous species to be analysed from said gas chromatograph to said oxidation oven;
means for transferring said gaseous species produced by heating from said oxidation oven to said laser isotopes analyser.

Moreover, the system preferably comprises at least the following components:
means for collecting and concentrating said gaseous species produced by heating before isotope analysis;
at least one processor suitable for controlling at least part of the components of said system.

It is to be noted that the present device foresees the following features:
said oxidation oven transforms said gas species to be analysed, at least into carbon dioxide $CO_2$;
said laser isotopes analyser is configured to analyse isotopes of carbon contained in carbon dioxide $CO_2$;
said gas chromatograph is connected to at least one flame ionization detector or FID, and intended to measure the retention times of gas species and to calibrate the system.

The preferred embodiment of the device is configured, by at least one known means, so as to be used with a process that comprises a sequence formed by the following steps (at least partially controlled by said processor and whereof at least two steps can be partially simultaneous):
a) part of a partially gaseous mixture enters said gas chromatograph;
b) said part of said mixture is partially separated into two portions, at least one partially gaseous species contained in one of these portions being different from at least one partially gaseous species contained in the other of said portions;
c) at least part of one of said portions enters said oxidation oven;
d) said oxidation oven heats said part of said portion, and then generates at least one partially gaseous species;
e) at least part of the latter generated species enters said laser analyser, which analyses the isotope content relative to a chemical element which constitutes a part of the same generated species;
f) steps c), d), e), are repeated for at least another of said portions.

The gas chromatograph of the preferred embodiment of the present device is constituted at least by the following components partially inside a heated chamber:
one valve (called "sample valve") for sampling gaseous mixture from drilling mud, along a line where said gaseous mixture flows continuously;
one conduit for the entry of at least a carrier gas (called "primary entry line") connected to at least one way of said sample valve;
one other conduit for the entry of the gaseous mixture to be analysed (called "gas entry line") connected to at least one way of said sample valve;
one other conduit which performs the function of chromatographic column (called "backwashing column") connected to at least two ways of said sample valve;
one other conduit (hereinafter, "sampling cell") where said gaseous mixture flows and where the same mixture is subsequently taken over by the carrier gas, said sampling cell being connected to at least two outlets or ways of said sample valve;
one other conduit (called "intermediate line") connected to at least one way of said sample valve;
said sample valve being able to place in contact at least:
said sampling cell with gas entry line and a discharge conduit, or said sampling cell at least with said backwashing column and said primary entry line;

said backwashing column with said primary entry line and with a discharge conduit, or said backwashing column with said intermediate line and said sampling cell;

said gas entry line with said sampling cell or with a discharge conduit;

one other valve (hereinafter, "storage valve") connected to the sample valve by means of said "intermediate line";

one other conduit for storing the gaseous species to be analyzed (hereinafter, "store column") connected to at least two ways of said storage valve;

said store column performing the function of a chromatographic column;

one other conduit (called "connection line") connected to at least one way of said storage valve;

said storage valve being able to place in contact at least:
said store column with said intermediate line and said connection line, or said store column with at least two partially closed sections;

a flame ionization analyser FID, connected to the system and in contact with said storage valve. Said FID carries out the synchronisation of the valves and monitors the output times of different gaseous species under examination in order to calibrate the device and to be sure that the same gaseous species are sent separately to the oxidation oven;

one other valve (called "final valve") connected to said storage valve through said connection line;

one other conduit for the final sampling of the gaseous species to be analysed, which is conveyed towards the oxidation oven by the carrier gas. Said conduit being referred to as "holding chamber" and connected to at least two ways of said final valve;

one other conduit for the discharge of gas, connected to at least one way of said final valve;

one other conduit for the entry of the carrier gas (called "secondary entry line") connected to at least one way of said final valve;

one other conduit (called "exit line") for the exit of each gas species travelling towards said oxidation oven, said exit line being connected to at least one way of said final valve;

said final valve being able to place in contact at least:
said holding chamber st with said connection line and a discharge conduit, or said holding chamber with said secondary entry line and said exit line;
said connection line with said holding chamber, or with a discharge conduit;

said valves being able to place in contact different pairs of outlets or ways according to the configuration which they assume, and being controlled preferably by solenoid valves via pressurised air;

said valves preferably being pneumatic.

During the analysis cycle, these valves change configuration automatically via the processor which controls said solenoid valves, and at instants of time. These valves are programmed in such a way that the gaseous species of interest arrive separated at the oxidation oven. The initial gaseous mixture, transiting via the backwashing and store columns (preferably filled with active polymers able to slow down most the motion of heavier gases), separates into the single gaseous species, which are sent singly to the oxidation oven due to synchronisation of the same valves.

Generically, the preferred embodiment of the present system is configured with adequate means so as to allow said chromatograph to be able to operate according to a process which comprises at least the sequence formed by the following steps—at least partially controlled by said processor, which in turn is preferably manually calibrated by the user, and whereof at least two steps can be at least partially simultaneous:

at least part of a partially gaseous mixture (henceforth, "mixture") arriving from the entry line for the gas, flows at least partially through the sampling cell and moves towards a discharge conduit;

said sample valve changes configuration so as to place said primary entry line in contact with said sampling cell;

at least a carrier gas partially enters the sampling cell, taking from it said part of the mixture, and drawing the latter at least partially into the backwashing column;

two or more partially gaseous species of said mixture (henceforth, "species") are at least partially separated, or moved away, between them and within said backwashing column;

at least a carrier gas starts to draw at least two of said species (henceforth, "first species" and "second species") are preferably the lighter components of said part of the mixture, inside said intermediate line;

after the heaviest species which is to be analysed has partially entered said intermediate line, the sample valve once again changes configuration, so as to prevent heavier species from entering said intermediate line;

at least one carrier gas draws said first and second species to be analyzed partially through said intermediate line and subsequently inside said store column, where the latter two species move away even more between them;

at least said first species exits from said store column, while said storage valve is places said store column in contact with said connection line, and enters said connection line;

said storage valve changes configuration so as to place said store column in contact with said two closed sections so that said second species remains trapped inside said store column;

at least one carrier gas draws said first species through said connection line, and subsequently inside said holding chamber, while said final valve places said holding chamber in contact with said connection line;

said final valve changes configuration so as to place said holding chamber in contact with said secondary entry line;

at least one carrier gas, arriving from said secondary entry line, flows through said holding chamber, taking said first species and conveying it into said exit line;

said storage valve changes configuration so as to place said store column in contact with said connection line so that said second species exits from said store column, and enters said connection line;

at least one carrier gas draws said second species through said connection line, and subsequently inside said holding chamber, while said final valve again places said holding chamber in contact with said connection line;

said final valve changes configuration so as to place said holding chamber in contact with said secondary entry line;

at least one carrier gas, arriving from said secondary entry line, flows through said holding chamber, taking said second species and conveying it into said exit line. It is to be considered that, if said at least two gaseous species to be analyzed are more than two, when the second species is in the holding chamber, another species (called "third species") remains trapped in the store column as a result of another configuration change of said storage valve.

The system is synchronized so that, separately and sequentially, for each single species of said at least two species:

the single species flows through said exit line, enters said oxidation oven and is heated so as to produce carbon dioxide;

the carbon dioxide produced by the heating of said single species is collected and concentrated by known means;

said isotope analyzer detects the isotopic content of the carbon contained in said carbon dioxide, which is derived from said single species.

All these features will be made clearer by the following detailed description of a possible embodiment of the present invention, to be considered by way of a non-limiting example of the more general concepts claimed.

BRIEF DESCRIPTION OF THE DRAWINGS

The following description refers to the accompanying drawings, in which:

FIG. 2 is an enlargement of the zone where the sample valve is disposed;

FIG. 3 is an enlargement of the zone where the storage valve is disposed;

FIG. 5 is a block diagram of the initial phase in which the entire system undergoes washing;

FIG. 6 is a block diagram of the phase during which the gaseous species to be analysed are taken by the carrier gas into the sampling cell;

FIG. 7 is a block diagram of the phase during which a single gaseous species is transported towards the oxidation oven.

DETAILED DESCRIPTION OF THE INVENTION

Figure 1:
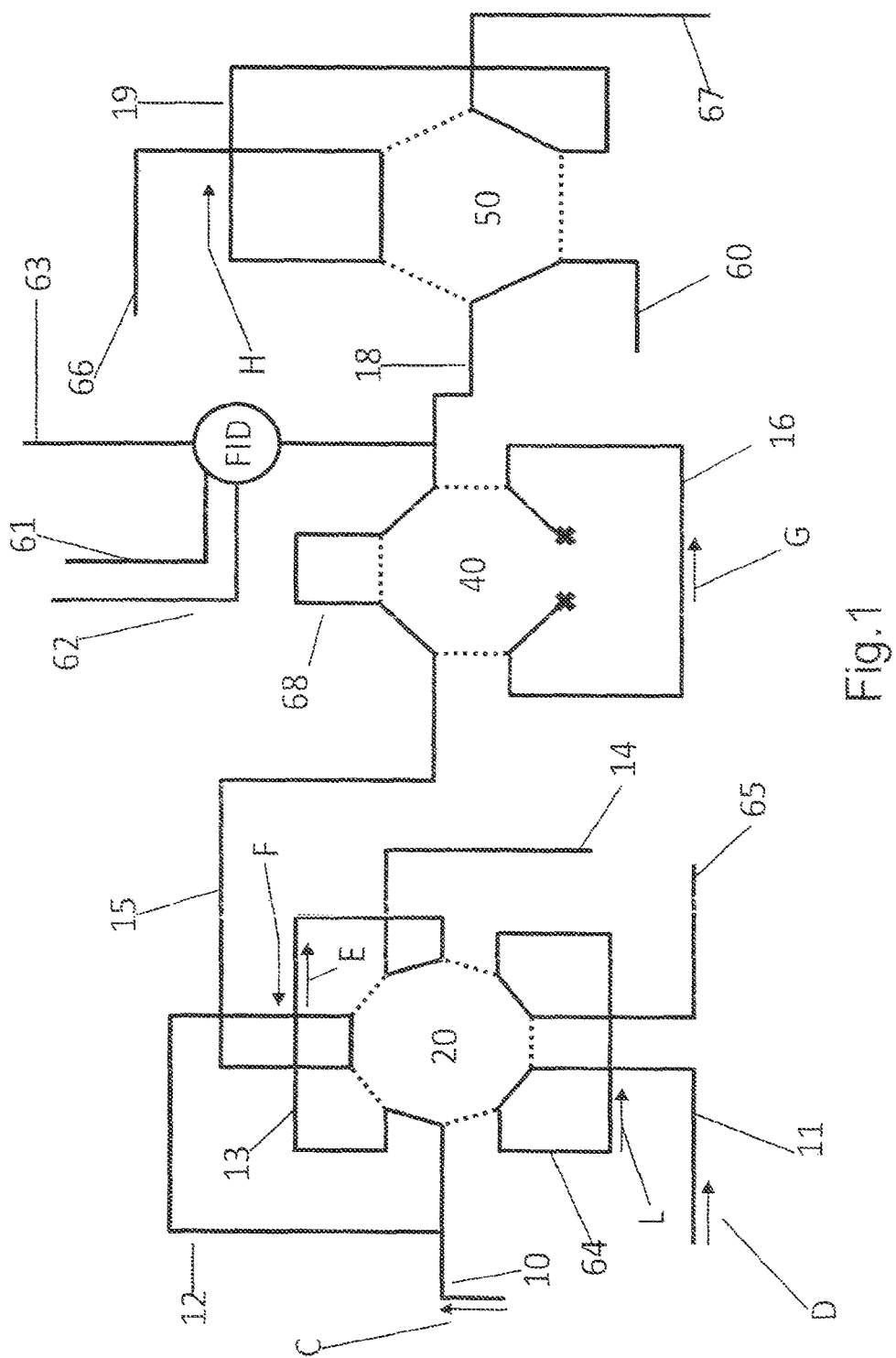
FIG. 1 is a schematic representation of the gas chromatograph analysis circuit.

In FIG. 1, the lines schematically represent conduits or columns where the gaseous species can transit and, as a general rule, when two lines intersect completely, forming four equal angles, two by two. The relative conduits are not in contact with each other. The carrier gas, preferably nitrogen $N_2$, comes in the direction of the arrow C from the primary entry line or conduit 10, while the gas to be analysed comes in the direction of the arrow D from the conduit or entry line for the gas 11, and can be a continuous flow or also only a sample.

Figure 4:
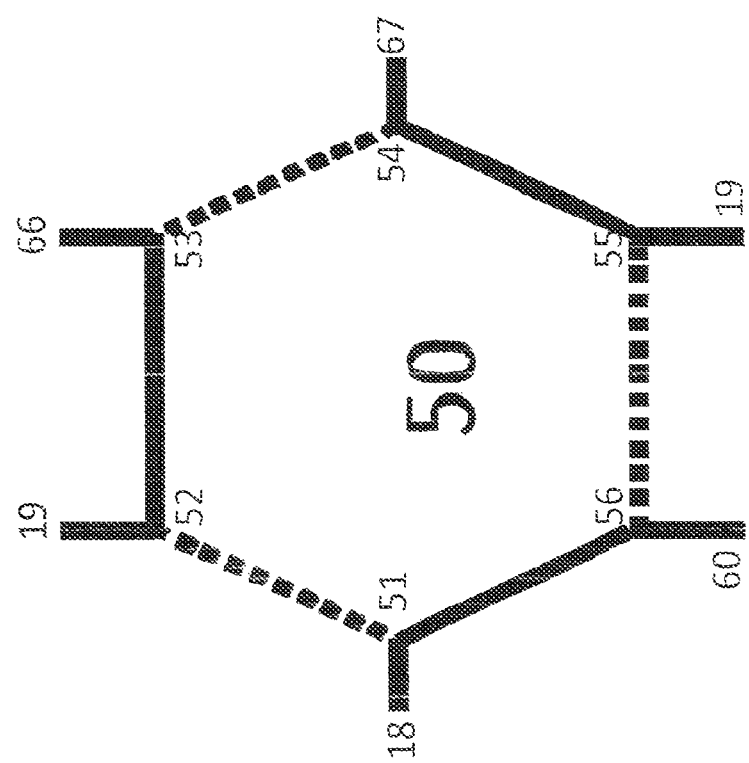
FIG. 4 is an enlargement of the zone where the final valve is disposed.

The three sample 20, storage 40 and final 50 valves can be seen, each of which, as can be seen also in FIGS. 2, 3 and 4, is provided with a certain number of ways or inlets, schematically positioned at the vertices of a polygon and corresponding, only in FIGS. 2, 3 and 4, to progressive series of numbers. Said valves can take on at least two configurations, such that when they take on the first configuration they place the pairs of ways in direct contact corresponding to the pairs of vertices between which a continuous line is placed, whereas when they take on the second configuration they place the pairs of ways in contact corresponding to the pairs of vertices represented by a dotted line. Henceforth said first configuration will be referred to as configuration "A" while said second configuration will be referred to as configuration "B".

In FIGS. 2, 3 and 4 some conduits connected to the valves are denoted by the corresponding number and, due to a space requirement, interrupted partially.

As can be seen in detail in FIG. 2, configuration A, the sample valve 20 places in contact:

the backwashing column 13 with the primary entry line 10 and a discharge line 14, thus respectively the pairs of ways 21, 30 and 25, 24;

the sampling cell 64 with the primary entry line for the gas 11 and a discharge conduit 65, thus respectively the pairs of ways 29, 28 and 26, 27;

the compensation conduit 12 with the intermediate line 15, thus the pairs of ways 23, 22;

whereas in configuration B, the sample valve 20 places in contact:

the backwashing column 13 with the sampling cell 64 and the intermediate line 15, thus respectively the pairs of outlets 25, 26 and 21, 22;

the entry line for the gas 11 with a discharge conduit 65, thus the pair of ways 28 and 27;

the sampling cell 64 with the primary entry line 10, thus the pair of outlets 29, 30;

the compensation conduit 12 with a discharge conduit 14, thus the pair of outlets 23, 24.

As can be seen in FIG. 3, in configuration A, for example, the storage valve 40 places in contact the store column 16 with the closed ways 46 and 47, thus respectively the pairs of ways 48, 47 and 45, 46; in configuration B, instead, it places the store column 16 in contact with the intermediate line 15 and the connection line 18, thus respectively the pairs of ways 48, 41 and 45, 44.

As can be seen in FIG. 4, in configuration A, for example, the final valve 50 places the holding chamber 19 in contact with the secondary entry line 66 and the exit line 67, thus respectively the pairs of ways 52, 53 and 55, 54; in configuration B, instead, it places the holding chamber 19 in contact with the connection line 18 and a discharge conduit 60, thus respectively the pairs of ways 52, 51 and 55, 56.

In this example, the eventuality that the gases of interest are methane $CH_4$, ethane $C_2H_6$ and propane $C_3H_8$, whereof the first is the lightest and the last one is the heaviest, is taken into consideration. The process whereby the instrument operates from when the gas enters the gas chromatograph to when the heaviest gas species exits, moving towards the oxidation oven, consists of several phases, which are preferably controlled by specific software.

In the first phase, the sampling valve 20 is set, automatically by the software, in configuration "A," while the storage 40 and final valves 50 are in configuration "B". In this way, part of the carrier gas which comes from the primary entry line 10, as can be seen in FIGS. 1 and 2, enters the way 30, exits from the way 21, and travels along the backwashing column 13 in the direction of arrow E. Afterwards, it enters the way 25 and exits from the way 24 to move towards a discharge conduit 14, thus cleaning said backwashing column 13.

The other part of the carrier gas, which branches off from the initial crossing, as can be seen in FIGS. 1 and 2, travels along the compensation conduit 12, enters the way 23, exits from the way 22 and moves, via the intermediate line 15, towards the storage valve 40.

Subsequently, as can be seen in FIGS. 1 and 3, the carrier gas enters the way 41 of said storage valve 40, then exits from the way 48 and subsequently travels in the direction of arrow G and cleans the store column 16. Subsequently, said part of carrier gas enters the way 45, exits from the way 44, and arrives at a crossing in which it divides into two portions.

The first of these portions is smaller, and reaches the flame ionization analyser or FID 17, which is therefore intended to calculate the arrival times of the various gaseous species, while the other one travels along the connection line 18, subsequently entering the way 51 of the final valve 50 as can be seen in FIG. 4. The latter portion then exits the way 52, travels in the direction of arrow H and cleans the holding chamber 19, so as to enter the way 55 and exit from the way 56, to then reach the discharge 60.

FIG. 1 also shows the supply lines to the FID of air 61 and hydrogen 62, as well as the discharge line for condensation 63.

As shown in FIGS. 1 and 2, the gas mixture to be analysed, comes from the entry line for the gas 11, enters the way 28, exits from the way 29, travels in the direction of arrow L along the sampling cell 64, enters the way 26 and exits, moving towards the discharge conduit 65, from the way 27.

The second phase starts up when the initial valve 20 changes configuration at the command of the synchronised processor, so that the portion of carrier gas which arrives at the way 30 is forced to travel along the sampling cell 64, passing from the way 29 and in the direction of arrow L, taking the gas content thereof. Subsequently this flow of carrier gas, together with the mixture collected, traverses the way 26, exits from the way 25 and travels along the backwashing column 13 in the direction of arrow F, to then pass through the ways 21 and 22 and flow into the intermediate line 15.

When the gases exit from the way 22, the gases are already at least partially separated because they have travelled along the backwashing column 13, which is a separation chromatographic column, i.e., it has the capacity to slow down most of the heavier gases. During this phase, the gaseous mixture, coming from the entry line for the gas 11, flows continuously in the case of continuous analysis. The gaseous mixture flows through the ways 28 and 27, directly towards the discharge conduit 65, in such a way that successive analyses are fairly faithful to the current depth.

The system is synchronised, preferably by means of the processor. This is done in such a way that the sample valve 20 returns to configuration A, triggering the third phase, when the gas species of interest (in this case methane, ethane and propane) are drawn into the intermediate line 15, so that they alone are transported towards the storage valve 40. Since propane is the heaviest gas, the sample valve 20 returns to configuration A when the entire propane portion has exited from the way 22. Methane and ethane are lighter, and are in a more advanced position, along said intermediate line 15, towards the storage valve 40.

During said third phase, the carrier gas returns to wash in the countercurrent from the backwashing column 13, cleaning the gaseous species from the backwashing column 13 that are not of interest, while the in-coming gaseous mixture continues to travel continuously along the sampling cell 64. The gaseous mixture then moves towards the discharge 65 to ensure that the analyses are correlated to depth at a reduced time lag. The compensation conduit 12 is so called because it serves to ensure that, in this phase, the carrier gas (which arrives from said compensation conduit 12 and flows into the intermediate line 15) arrives with the same load losses whereto the flow of carrier gas was subject. In the previous phase, the carrier gas flowed into said intermediate line 15 after having travelled along the backwashing column 13.

Methane, which is the lightest of the three gases, arrives first at the storage valve 40 and traverses (as seen in FIGS. 1 and 3) the ways 41 and 48 sequentially—said storage valve 40 being in configuration B—to then enter the store column 16. Subsequently, Methane enters the way 45 and exits definitively from said storage valve 40 through the way 44, to then move towards the FID in part and the final valve 50 in part.

The first of said parts, which is usually smaller, only serves to calculate the arrival times of the various gases during calibration and synchronise the valves, preferably by means of the processor and preferably manually by the user. On the other hand, the second of said parts travels along the connection line 18 and arrives at the final valve 50. Said part of methane (as shown in FIGS. 1 and 4) enters the way 51 and exits from the way 52—said final valve 50 being in configuration B—to then travel along the holding chamber 19.

When all the methane is inside the holding chamber 19, the storage valve 40 passes automatically into configuration A, as a result of the synchronised processor, so as to trap ethane and propane in the store column 16. The store column 16 is in direct contact with the closed ways 47 and 46 in this case, as can be seen in FIG. 2. This condition is known as "store column" and corresponds with the fourth phase, during which the carrier gas that arrives from the intermediate line 15 traverses the valve 68 (referred to as "tap valve") connected to the ways 42 and 43 of the storage valve 40. After the carrier gas flows into the connection line 18, the carrier gas enters the discharge line 60, and passes through the final valve 50 (as seen in FIG. 1).

During the successive fifth phase, the final valve 50 also takes on configuration A, so that the carrier gas that arrives from the secondary entry line 66 (as seen in FIGS. 1 and 4) travels along said holding chamber 19 after having traversed the ways 53 and 52. The carrier gas can then take on the methane located in said holding chamber 19. Subsequently, the methane is transported into the exit line 67, passing through the ways 55 and 54, and heads for the oxidation oven.

In the sixth phase, the storage 40 and final 50 valves are once again in configuration B, so that the carrier gas coming from the holding chamber 19 travels to the discharge 60, passing sequentially through the ways 55 and 56 of said final valve 50. On the other hand, ethane, which is trapped in the storage column 16, can travel towards the final valve 50 and the FID 17. The system is preferably synchronised so that until all the ethane reaches the holding chamber 19, the propane, which is heavier, does not yet travel along the entire store column 16. In this way, the previous trapping effect acts effectively only on the portion of ethane.

The seventh phase starts when, the storage valve 40 moves into configuration A at the moment at which all the ethane is in the holding chamber 19. This traps the propane in the store column 16, restoring the condition of "store column". Subsequently, the final valve 50 also moves into configuration A, triggering the eighth phase.

In the eighth phase, the carrier gas coming from the secondary line 66 conveys the ethane towards the oxidation oven through the exit line 67.

In phase nine phase, both the storage 40 and final 50 valves are again in configuration B. Thanks to the flow of carrier gas arriving from the intermediate line 15, a portion of propane flows towards the final valve 50 through the connection line 18, while the other portion of this gas moves towards the FID, which calibrates the retention times.

Phase ten starts when the final valve 50 takes on configuration A (i.e., after the entire portion of propane heading for the final valve 50 has entered the holding chamber 19). Said portion is conveyed by the carrier gas coming from the secondary entry line 66 (as seen in FIG. 4) into the exit line 67, and then drawn towards the oxidation oven.

In phase eleven, the final valve 50 is once again in configuration B. The system therefore returns to the initial conditions and the analysis sampling cycle begins again.

All valve configuration changes are managed by the processor, so that the user only has to start the instrument, which is controlled by software. The phase of preliminary calibration, and therefore of software programming, is preferably performed manually by the user.

In FIG. 5, the second phase is schematised. It shows the carrier gas, $N_2$, entering the sampling cell, taking the gas species indicated as $C_1$, $C_2$, and $C_3$, and transporting them to the store column. The other portion of carrier gas travels along the compensation conduit to the discharge.

In FIG. 6, the third phase is schematised, during which $C_1$, the lightest of the gases to be analysed (i.e., methane) is transported into the holding chamber, while $C_2$ and $C_3$ remain trapped in the store column. The path of the incoming carrier gas can be seen, part of which washes in against the backwashing column to then go to the discharge. Another part of the carrier gas travels along the compensation conduit, entering the store column and drawing the lightest of the gases towards the holding chamber and the FID.

FIG. 7 schematises the fifth phase, during which the carrier gas coming from the secondary entry line enters the holding chamber, takes the content of $C_1$, and transports the gas to the oxidation oven.

Said gas is transformed preferably into carbon dioxide which, after having passed through a sampler that collects the gas and concentrates it, goes to an isotopes analyser (preferably laser) that is configured appropriately and whose functions are known in the art. Said analyser is mainly based on detecting light absorption by atoms $^{12}C$ and $^{12}C$ at two different wavelengths. The configuration has to be regulated especially on the basis of the gas to be analysed, in our case $CO_2$.

Variations in the constitution of the system described and of the process whereby it operates are possible, in any case coming within the scope of protection of the present patent according to what is expressed in the claims.

What is claimed is:

1. A method for measurement of isotopic content of at least two partially gaseous species derived from a mixture extracted from drilling mud, comprising the following steps:

(a) in a first phase, one part of at least one carrier gas comes from a primary entry line, enters a sample valve of a gas chromatograph through one way and exits from another way, travels along a backwashing column, enters the sample valve one way and exits from another way, then moves towards a discharge conduit; another part of said at least one carrier gas comes from the primary entry line, travels along a compensation conduit, enters the sample valve one way and exits from another way, travels along an intermediate line, enters a storage valve one way and exits from another way, travels along a store column, enters the storage valve one way and exits from another way, arrives at a crossing in which said other part of said at least one carrier gas divides into two portions, a first of said two portions reaching a flame ionisation analyser and a second of said two portions travels along a connection line, enters a final valve one way and exits from another way, clearing a holding chamber by entering the final valve one way and exiting from another way, and reaching a discharge conduit; wherein said mixture comes from an entry line and contains at least a first species, a second species and third species, said third species being heavier than the first and the second species, enters the sample valve one way and exits from another way, travels along the sampling cell, enters the sample valve one way and exits from another way, then moves towards a discharge conduit;

(b) in a second phase, starting when the sample valve changes configuration by means of a processor, one part of said at least one carrier gas comes from the primary entry line, enters the sample valve one way and exits from another way, travels along the sampling cell collecting the mixture thereof, enters the sample valve one way and exits from another way, travels along the backwashing column, enters the sample valve one way and exits from another, and travels along the intermediate line, said backwashing column being a chromatographic column separating the at least two gaseous species of the mixture, the first species being in a more advanced position than the second species along said intermediate line; said mixture comes from an entry line entering the sample valve one way and exiting from another, moving towards a discharge conduit;

(c) in a third phase, starting when the sample valve changes configuration again by means of said processor, said mixture, coming from the intermediate line, enters the storage valve one way and exits from another way, and enters the store column, the first species entering first in said store column; the first species enters the storage valve one way and exits from another way, arrives at a crossing in which said first species divides into two portions, the first of said two portions reaching a flame ionisation analyser, and the second of said two portions travels along the connection line, entering one way of the final valve and exits from another way, and travels along the holding chamber;

(d) in a fourth phase, starting when the storage valve changes configuration by means of said processor, so that the second species remains trapped in said store column, and all the first species is inside the holding chamber, carrier gas coming from the intermediate line, enters the storage valve one way and exits from another way, traverses a tap valve, enters the storage valve one way and exits from another way, flows into the connection line, enters the final valve one way and exits from another way, and enters a discharge conduit;

(e) in a fifth phase, starting when the final valve changes configuration by means of said processor, carrier gas coming from the secondary entry line, enters the final valve one way and exits from another way, travels along said holding chamber, takes said first species located in said holding chamber, enters the final valve one way and exits from another way, flows through an exit line, reaches an oxidation oven, is heated to produce carbon dioxide, the isotopic content of said carbon dioxide being analysed by an isotope analyzer;

(f) in a sixth phase, starting when the storage valve and the final valve change configuration by means of said processor, carrier gas coming from the holding chamber enters the final valve one way and exits from another way, travels to a discharge; the second species enters the storage valve one way and exits from another way, arrives at a crossing in which said second species divides into two portions, the first of said two portions reaching a flame ionisation analyser and the second of said two portions travels along the connection line, enters the final valve one way and exits from another way, and travels along the holding chamber;

(g) in a seventh phase, starting when the storage valve changes configuration by means of said processor so that the third species remains trapped in said store column, said storage valve changes configuration when all the second species is inside the holding chamber;

(h) an eight phase, starting when the final valve changes configuration by means of said processor, carrier gas coming from the secondary entry line enters the final valve one way and exits from another way, travels along said holding chamber, takes said second species located in said holding chamber, enters the final valve one way and exits from another way, flows through the exit line, reaches the oxidation oven, and is heated to produce carbon dioxide;

(i) in a ninth phase, starting when the storage valve and the final valve change configuration by means of said processor, the third species enters the storage valve one way and exits from another way, arrives at a crossing in which said third species divides into two portions, the first of said two portions reaching a flame ionisation analyser, and the second of said two portions travels along the connection line, enters the final valve one way and exits from another way, and travels along the holding chamber;

(j) in a tenth phase, starting when the final valve changes configuration by means of said processor, carrier gas coming from the secondary entry line, enters the final valve one way and exits from another way, travels along said holding chamber, takes said third species located in said holding chamber, enters the final valve one way and exits from another way, flows through the exit line, reaches the oxidation oven, and is heated to produce carbon dioxide; and (k) in an eleventh phase, the final valve changes configurations again by means of said processor to end the measurement of the isotopic content of the at least two partially gaseous species to begin anew.

\* \* \* \* \*